United States Patent
Coats et al.

(10) Patent No.: US 9,955,940 B1
(45) Date of Patent: May 1, 2018

(54) ECHOGENIC NERVE BLOCK CATHETER AND ECHOGENIC CATHETER TIP

(75) Inventors: Alfred C. Coats, Houston, TX (US); Louis Lupin, Houston, TX (US); Paul E. Bigeleisen, Pittsford, NY (US)

(73) Assignee: Avent, Inc., Alpharetta, GA (US)

( * ) Notice: Subject to any disclaimer, the term of this patent is extended or adjusted under 35 U.S.C. 154(b) by 0 days. days.

(21) Appl. No.: 13/093,562

(22) Filed: Apr. 25, 2011

Related U.S. Application Data

(60) Provisional application No. 61/327,316, filed on Apr. 23, 2010.

(51) Int. Cl.
*A61M 25/00* (2006.01)
*A61B 19/00* (2006.01)
*A61B 8/00* (2006.01)
*A61B 90/00* (2016.01)

(52) U.S. Cl.
CPC ........ *A61B 8/00* (2013.01); *A61B 2090/3925* (2016.02)

(58) Field of Classification Search
USPC ........................................................ 600/439
See application file for complete search history.

(56) References Cited

U.S. PATENT DOCUMENTS

| | | | |
|---|---|---|---|
| 4,401,124 A | 8/1983 | Guess et al. | |
| 4,582,061 A | 4/1986 | Fry | |
| 5,259,837 A | 11/1993 | Van Wormer | |
| 5,490,845 A | 2/1996 | Racz | |
| 5,899,891 A | 5/1999 | Racz | |
| 5,921,933 A | 7/1999 | Sarkis et al. | |
| 5,967,988 A | 10/1999 | Briscoe et al. | |
| 6,053,870 A | 4/2000 | Fulton, III | |
| 6,749,554 B1 | 6/2004 | Snow et al. | |
| 8,226,544 B2 | 7/2012 | Muyari et al. | |
| 8,342,795 B2 | 1/2013 | Hodapp | |
| 2002/0082546 A1* | 6/2002 | Crank et al. | 604/48 |
| 2004/0049231 A1* | 3/2004 | Hafer | 607/3 |
| 2005/0033334 A1 | 2/2005 | Santra et al. | |
| 2007/0179471 A1* | 8/2007 | Christian et al. | 604/523 |
| 2008/0154136 A1* | 6/2008 | Webler | 600/463 |
| 2009/0143764 A1* | 6/2009 | Nelson | A61M 5/14276 604/510 |
| 2009/0177114 A1* | 7/2009 | Chin et al. | 600/565 |

FOREIGN PATENT DOCUMENTS

| | | |
|---|---|---|
| DE | 2425724 | 11/1974 |
| WO | WO 2006/044374 A1 | 4/2006 |
| WO | WO/2007/067324 | 6/2007 |

OTHER PUBLICATIONS

"A New Echogenic Needle for Ultrasound Guided Nerve Block", Bigeleisen, Paul E., M.D., Presbyterian Hospital, University of Pittsburgh, A poster displayed Dec. 2006 at the New York Society of Anesthessology Post Graduate Assembly.

* cited by examiner

*Primary Examiner* — Patricia Park
(74) *Attorney, Agent, or Firm* — Dority & Manning, P.A.

(57) ABSTRACT

An echogenic nerve block catheter and an echogenic catheter tip member include an echogenic tip member having a plurality of ridges on a first portion of the tip member and a retainer member is on a second portion of the tip member, and the second portion of the tip member is received within the lumen of the nerve block catheter.

17 Claims, 1 Drawing Sheet

ECHOGENIC NERVE BLOCK CATHETER AND ECHOGENIC CATHETER TIP

BACKGROUND OF THE INVENTION

1. Related Application

This Application claims the benefit, and priority benefit, of U.S. Patent Application Ser. No. 61/327,316, filed Apr. 23, 2010, entitled "Echogenic Nerve Block Catheter and Echogenic Catheter Tip".

2. Field of the Invention

The invention relates to nerve block catheters, including echogenic nerve block catheters and echogenic nerve block catheters that are also capable of delivering an electrical pulse at the tip of the catheter.

3. Description of the Related Art

Anesthesiologists prolong nerve block anesthesia into the post-operative period of a procedure by running a small catheter through a hypodermic needle used to deliver a local anesthetic, and then pulling the needle out while leaving the catheter in place. The catheter is then attached to a infusion pump that continuously delivers anesthetic. In performing nerve block anesthesia, anesthesiologists may use ultrasound imaging to help guide the needle to the target nerve, but ultrasound imaging of continuous nerve block catheters is suboptimal in helping to localize, or position, the tip of the nerve block catheter with respect to the target nerve.

SUMMARY OF THE INVENTION

In illustrative embodiments of the present echogenic nerve block catheter, the echogenic nerve block catheter may include a catheter having a longitudinal axis, a distal end, a proximal end, and a lumen extending from the distal end toward the proximal end; and an echogenic catheter tip member may have a longitudinal axis, an outer surface, a first portion extending outwardly from the distal end of the catheter, and a second portion received within the lumen of the catheter.

In accordance with another aspect of an illustrative embodiment of the present echogenic catheter tip member, the echogenic catheter tip member, for use with a nerve block catheter having a longitudinal axis, a distal end, a proximal end, and a lumen extending from the distal end toward the proximal end, may include a tip member having a longitudinal axis, an outer surface, a first portion adapted to extend outwardly from the distal end of the lumen of the catheter, and a second portion adapted to be received within the lumen of the catheter. A plurality of ridges may be disposed on the outer surface of the first portion of the echogenic catheter tip member, and at least one of the ridges may be disposed in a plane that is substantially perpendicular to the longitudinal axis of the echogenic catheter tip member. At least one of the ridges may have a top outer surface, and the top outer surface may have a substantially triangular or rectangular configuration.

BRIEF DESCRIPTION OF THE DRAWING

The present echogenic nerve block catheters and echogenic catheter tips may be understood by reference to the following description taken in conjunction with the accompanying drawing, in which.

Figure 1:
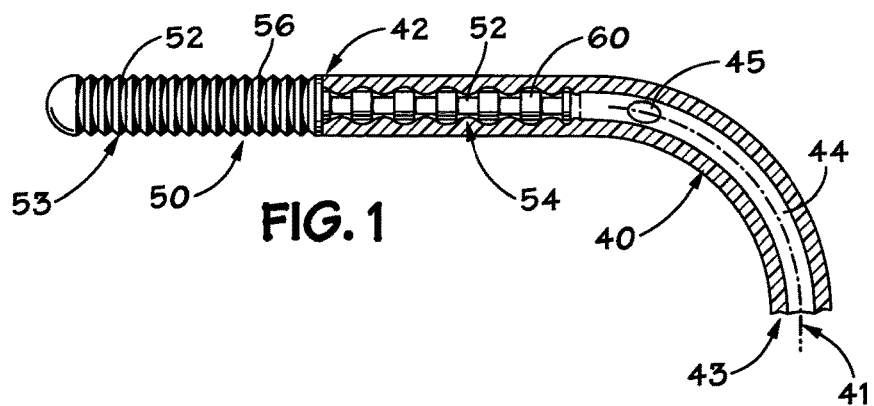
FIG. 1 is a partial cross-sectional side view of an embodiment of the present echogenic nerve block catheter.

While certain embodiments of the present echogenic nerve block catheter and echogenic catheter tip will be described in connection with the preferred illustrative embodiments shown herein, it will be understood that it is not intended to limit the invention to those embodiments. On the contrary, it is intended to cover all alternatives, modifications, and equivalents, as may be included within the spirit and scope of the invention as defined by the appended claims. In the drawing figures, which are not to scale, the same reference numerals are used throughout the description and in the drawing figures for components and elements having the same structure, and primed reference numerals may be used for components and elements having a similar function and construction to those components and elements having the same unprimed reference numerals.

DETAILED DESCRIPTION OF THE ILLUSTRATIVE EMBODIMENTS

Figure 2:
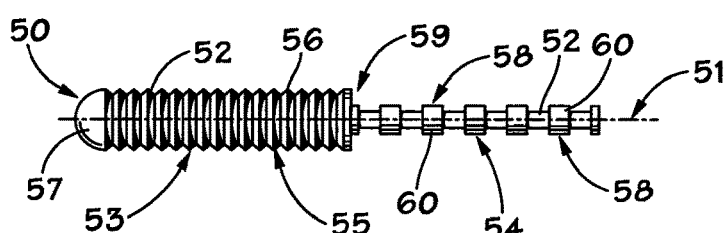
FIG. 2 is a side view of an echogenic catheter tip for use in the nerve block catheter of FIG. 1.

As shown in FIGS. 1 and 2, the present echogenic nerve block catheter generally comprises a nerve block catheter, or catheter, 40 with an echogenic catheter tip, or echogenic catheter tip member 50, associated with the distal end 42 of the catheter 40 as by inserting it into the distal end 42 of the catheter. The nerve block catheter, or catheter, 40 may be of conventional construction and formed of a suitable plastic material, such as polyurethane, and includes a longitudinal axis 41, a distal end 42, a proximal end 43, and a lumen 44 extending from the distal end 42 toward the proximal end 43 of the catheter 40. The catheter 40 may include a catheter eye 45, or a plurality of catheter eyes, which permit the anesthetic to pass outwardly from the catheter lumen 44 into the desired location in the patient (not shown). The echogenic catheter tip member 50 is preferably formed of a metallic material, stainless steel being preferred; however, any other suitable materials which are capable of providing the requisite echogenicity to the echogenic catheter tip member 50, may be utilized. A stainless steel rod may be used for tip member 50. The echogenic catheter tip member 50 preferably includes a longitudinal axis 51 (FIG. 2), an outer surface 52, a first portion 53 extending outwardly from the distal end 42 of the catheter 40, and a second portion 54 received within the lumen 44 of the catheter 40.

The outer surface 52 of the first portion 53 of the echogenic catheter tip member 50, or tip member, may have a plurality of ridges 55 disposed on the outer surface 52 of the first portion 53 of the echogenic catheter tip member 50. At least one of the ridges 55, and preferably all of the ridges 55, are disposed in a plane which is substantially perpendicular to the longitudinal axis 51 of the echogenic catheter tip member 50, as seen in FIG. 2. Preferably, the ridges 55 extend around the outer surface 52, or annular periphery of the tip member 50. As seen in FIGS. 1 and 2, at least one of the ridges 55, and preferably all of the ridges 55, have a top outer surface 56 and the top outer surface 56 of each ridge member has a substantially triangular configuration, as shown in FIGS. 1 and 2. Alternatively, the top outer surface 56 of each ridge member may have a substantially rectangular configuration, on any other periodic pattern of ridges 55 which provides the requisite echogenicity to the tip 50.

The tip member ridges 55, or pattern of ridges, may be machined into its outer wall 52, or outer surface, to provide echogenicity to the tip 50, whereby the catheter tip 50 reflects high frequency sound waves and may be imaged and viewed by conventional ultrasound imaging devices and equipment. The echogenic catheter tip 50 presents a contrasting acoustic impedance boundary from body tissue and reflects sound waves efficiently.

As shown in FIG. 2, the first portion 53 of the echogenic catheter tip 50 has a rounded distal end 57 to facilitate insertion of the echogenic nerve block catheter 40, 50 within the patient's body. On the outer surface 52 of the second portion 54 of the tip member 50 is disposed at least one retaining member 58. Preferably, a plurality of retaining members 58 are disposed on the outer surface 52 of the second portion 54 of the tip member 50. The at least one retaining member 58 is disposed adjacent the proximal end 59 (FIG. 2) of the tip member 50. Preferably, the second portion 54 of the echogenic catheter tip member 50 is secured to the lumen 44 of the catheter 40 as by use of a suitable adhesive or by a friction fit between the outer surface of the second portion 54 of the catheter tip 50 and inner wall surface of the lumen 44 of the catheter 40. The echogenic catheter tip 50 has at its proximal end 59 a pin structure, or insertion pin, with at least one, and preferably a plurality of, wide annular ridges 60, or retaining members 58, to facilitate the attachment and retention of the echogenic catheter tip 50 within the distal end of the nerve block catheter 40.

The present echogenic catheter tip 50 is compatible with a very small diameter nerve block catheter 40. Its echogenic area, or ridges 55, is located at the very tip, or distal end 42, of the catheter 40, which is the part of the nerve block catheter 40 that the anesthesiologist needs to locate with respect to its location within a patient's body. Its echogenic feature, or area, or ridges 55, is preferably constructed out of a solid rod, such as a rod of stainless steel, which allows a three-dimensional echogenic area, such as the first portion 53 of tip member 50, or ridges 55, to be placed in a very small volume. Its echogenic surface is not covered by the nerve block catheter's 40 plastic wall forming the lumen 44, which avoids an echogenicity-impairing plastic layer between the echogenic surface of the echogenic catheter tip 50 and body tissues.

Figure 3:
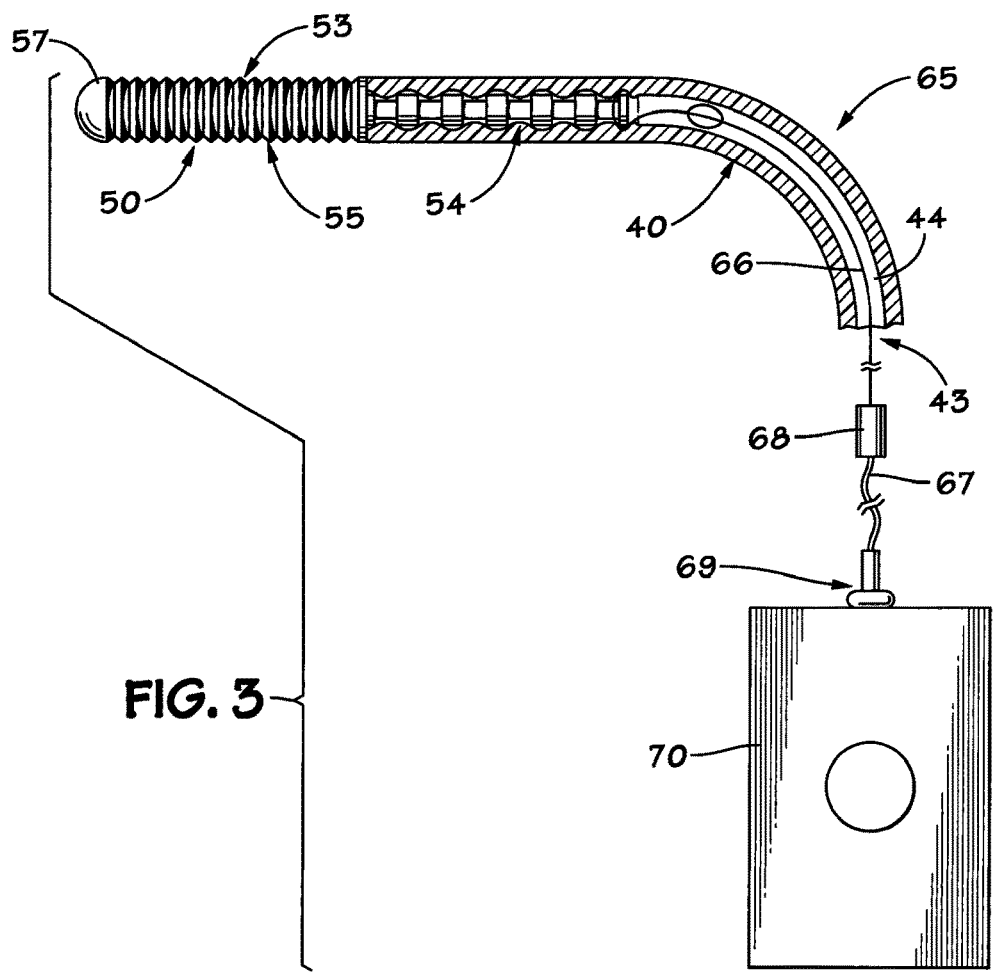
FIG. 3 is a partial cross-sectional side view of another embodiment of the present echogenic nerve block catheter, including nerve stimulating capability.

With reference to FIG. 3, the illustrative embodiment of echogenic nerve block catheter 65 shown allows an electrical pulse to be delivered at the catheter tip 50 to permit an anesthesiologist to confirm that the catheter tip 50 is close to the target nerve to be supplied with the anesthetic. If the electrical pulse elicits a twitch of the muscle controlled by the target nerve, correct placement of the catheter tip 50 is confirmed. A fine wire 66 may be attached to the second portion 54, or insertion pin, of the echogenic nerve block catheter's 40 echogenic catheter tip 50 and the wire 66 runs down, or passes through, the catheter lumen 44 to the catheter's proximal end 43. At the catheter's proximal end 43, the fine wire 66 may be connected to a standard electrical wire 67 as by any suitable connector 68. The standard electrical wire 67 may be connected via a standard electrical connector 69 to a nerve stimulator 70, which generates electrical pulses that provide the stimulus to the target nerve.

If desired, a fluid passageway may be provided within the catheter tip member 50. Preferably, such a fluid passageway (not shown) is disposed coincident with the longitudinal axis 51 of the tip member 50, to permit the anesthetic to pass outwardly from the catheter lumen 44, through the tip member 50 and exiting from the rounded distal end 57 of the tip member 50 to the desired nerve.

Specific illustrative embodiments of the present echogenic nerve block catheter and echogenic catheter tip have been described and illustrated. It will be understood to those skilled in the art that changes and modifications may be made without departing from the spirit and scope of the inventions defined by the appended claims.

We claim:

1. An echogenic nerve block catheter, comprising:
    a catheter having a longitudinal axis, a distal end, a proximal end, and a lumen extending from the distal end toward the proximal end; and
    an echogenic catheter tip member having a longitudinal axis, an outer surface, a first portion extending outwardly from the distal end of the catheter, a second portion received within and secured to the lumen of the catheter, a flange fixed to a proximal end of the first portion between the first portion and the second portion, and a plurality of ridges disposed on an outer surface of the first portion of the echogenic catheter tip member, the plurality of ridges defining an outermost diameter of the first portion that is greater than a diameter of the lumen,
    wherein the first portion comprises a rounded distal end, the flange having an outermost diameter that is equal to the outermost diameter of the first portion and greater than the diameter of the lumen such that the flange abuts against the distal end of the catheter when the second portion is received within the lumen, the outermost diameter of the flange and an outermost diameter of the first portion being equal.

2. The echogenic nerve block catheter of claim 1, wherein at least one of the plurality of ridges is disposed in a plane which is perpendicular to the longitudinal axis of the echogenic catheter tip member.

3. The echogenic nerve block catheter of claim 2, wherein the at least one ridge extends around the outer surface of the echogenic catheter tip member.

4. The echogenic nerve block catheter of claim 1, wherein at least one of the plurality of ridges has a top outer surface, the top outer surface having a triangular configuration.

5. The echogenic nerve block catheter of claim 1, wherein at least one of the plurality of ridges has a top outer surface, the top outer surface having a rectangular configuration.

6. The echogenic nerve block catheter of claim 1, wherein at least one retaining member is disposed on the outer surface of the second portion of the echogenic catheter tip member.

7. The echogenic nerve block catheter of claim 6, wherein the at least one retaining member is at least one annular ridge.

8. The echogenic nerve block catheter of claim 1, further comprising a wire attached to the echogenic catheter tip member, the wire extending through the lumen of the catheter and adapted to permit an electrical pulse to be delivered by the echogenic catheter tip member.

9. An echogenic catheter tip member, for use with a nerve block catheter having a longitudinal axis, a distal end, a proximal end, and a lumen extending from the distal end toward the proximal end, comprising:
    a tip member having a longitudinal axis, an outer surface, a first portion adapted to extend outwardly from the distal end of the lumen of the catheter, a second portion adapted to be received within and secured to the lumen of the catheter, the first portion having a rounded distal end, a flange fixed to a proximal end of, the first portion between the first portion and the second portion, and a plurality of ridges disposed on an outer surface of the first portion of the echogenic catheter tip member, the plurality of ridges defining an outermost diameter of the first portion that is greater than a diameter of the lumen;

an outer surface of the second portion of the tip member comprising at least one retaining member adapted to retain the second portion within the lumen of the catheter;

wherein the flange has an outermost diameter that is equal to the outermost diameter of the first portion and greater than the diameter of the lumen such that the flange abuts against the distal end of the catheter when the second portion is received within the lumen, the outermost diameter of the flange and an outermost diameter of the first portion being equal.

10. The echogenic catheter tip member of claim 9, wherein at least one of the ridges is disposed in a plane which is perpendicular to the longitudinal axis of the echogenic catheter tip member.

11. The echogenic catheter tip member of claim 9, wherein the at least one ridge extends around the outer surface of the echogenic catheter tip member.

12. The echogenic catheter tip member of claim 9, wherein at least one of the ridges has a top outer surface and the top outer surface has a triangular configuration.

13. The echogenic catheter tip member of claim 9, wherein at least one of the ridges has a top outer surface and the top outer surface has a rectangular configuration.

14. The echogenic catheter tip member of claim 9, wherein at least one retaining member is at least one annular ridge.

15. The echogenic catheter tip member of claim 9, including a wire attached to the echogenic catheter tip member, the wire extending through the lumen of the catheter, and adapted to permit an electrical pulse to be delivered by the echogenic tip member.

16. An echogenic nerve block catheter, comprising:
a catheter having a longitudinal axis, a distal end, a proximal end, and a lumen extending from the distal end toward the proximal end; and
an echogenic catheter tip member having a longitudinal axis, an outer surface, a first portion extending outwardly from the distal end of the catheter, a second portion received within and secured to the lumen of the catheter, the first portion having a rounded distal end, wherein a plurality of ridges are disposed on the outer surface of the first portion of the echogenic catheter tip member, the plurality of ridges defining an outermost diameter of the first portion that is greater than a diameter of the lumen, and wherein at least one of the ridges is disposed in a plane which is perpendicular to the longitudinal axis of the echogenic catheter tip member;

wherein a flange is fixed to a proximal end of the first portion between the first portion and the second portion, the flange having an outermost diameter that is equal to the outermost diameter of the first portion and greater than the diameter of the lumen such that the flange abuts against the distal end of the catheter when the second portion is received within the lumen, the outermost diameter of the flange and an outermost diameter of the first portion being equal.

17. An echogenic nerve block catheter, for use with a nerve block catheter having a longitudinal axis, a distal end, a proximal end, and lumen extending from the distal end toward the proximal end, comprising:
a tip member having a longitudinal axis, an outer surface, a first portion adapted to extend outwardly from the distal end of the lumen of the catheter, a second portion adapted to be received within and secured to the lumen of the catheter, and a plurality of ridges disposed on an outer surface of the first portion of the tip member, the first portion having a rounded distal end, the plurality of ridges defining an outermost diameter of the first portion that is greater than a diameter, of the lumen;
wherein at least one of the ridges is disposed in a plane which is perpendicular to the longitudinal axis of the echogenic catheter tip member; and
on the outer surface of the second portion of the tip member at least one retaining member is disposed and is adapted to retain the second portion within the lumen of the catheter;
wherein a flange is fixed to a proximal end of the first portion between the first portion and the second portion, the flange having an outermost diameter that is equal to the outermost diameter of the first portion and greater than the diameter of the lumen such that the flange abuts against the distal end of the catheter when the second portion is received within the lumen, the outermost diameter of the flange and an outermost diameter of the first portion being equal.

\* \* \* \* \*